United States Patent [19]

Hsieh

[11] 4,444,694

[45] Apr. 24, 1984

[54] PREPARATION OF 2-AMINOALKANESULFONIC ACID

[75] Inventor: Hsin H. Hsieh, Baton Rouge, La.

[73] Assignee: The Dow Chemical Company, Midland, Mich.

[21] Appl. No.: 487,478

[22] Filed: Apr. 22, 1983

[51] Int. Cl.$^3$ ............................................. C07C 143/02
[52] U.S. Cl. ................................................. 260/513 B
[58] Field of Search ........................ 260/513 B, 513 N

[56] References Cited

FOREIGN PATENT DOCUMENTS 1229542  12/1966  Fed. Rep. of Germany ... 260/513 B

Primary Examiner—Alan Siegel
Attorney, Agent, or Firm—Norman L. Sims

[57] ABSTRACT

The invention is a process for the preparation of the metal salt of 2-aminoalkanesulfonic acid which comprises contacting a 2-oxazolidinone with a water-soluble metal sulfite or a water-soluble metal hydrogen sulfite in aqueous solution under conditions such that a metal salt of 2-aminoethanesulfonic acid is prepared.

17 Claims, No Drawings

PREPARATION OF 2-AMINOALKANESULFONIC ACID

BACKGROUND OF THE INVENTION

This invention relates to a novel process for the preparation of 2-aminoalkanesulfonic acids (commonly known as taurines). More specifically, this invention relates to the preparation of the metal salts of the 2-aminoalkanesulfonic acids which can be converted to the acid form readily.

2-Aminoalkanesulfonic acids are useful in treating epilepsy and as intermediates in the preparation of N-acyl-N-alkyltaurates which are anionic surfactants with several advantageous properties.

2-Aminoethanesulfonic acid occurs in the tissues of various lower animals and in the secretions of higher animals. Common sources are ox bile and the large muscle of the abalone.

2-Aminoethanesulfonic acid has been synthesized by several methods. Kolbe, Ann., 122, 42 (1862), converted isethionic to 2-chloroethyl sulfonyl chloride, hydrolyzed this product to 2-chloroethyl sulfonic acid and obtained 2-aminoethanesulfonic acid by treating the 2-chloroethyl sulfonic acid with aqueous ammonia. In this process, the separation of the product from ammonium chloride is quite troublesome.

Gabriel, Ber., 21, 2667 (1888), prepared 2-aminoethanesulfonic acid from ethyleneimine and sulfur dioxide, and from 2-mercaptothiazoline by oxidation with bromine water, Ber., 22, 1153 (1884). Reychler, Bull. Soc. Chim. Belg., 32, 247 (1923), prepared 2-aminoethanesulfonic acid from bromoethylamine and ammonium sulfide. These methods require 2-bromoethylamine as a starting material and are not useful for the preparation of large amounts of the product.

Auzies, Chem. Zentr., 82 (II) 1433 (1911), prepared 2-aminoethanesulfonic acid by sulfonation of acetaldehyde with chlorosulfonic acid, followed by the reaction with ammonia to form the amido compound and finally by reduction to the amino compound. These reactions are complex.

Marvel et al., "A Synthesis of Taurine", J.A.C.S., 49, 1833 (1927) teach that 2-bromoethyl sulfonyl chloride is hydrolyzed to the acid form, then treated with aqueous ammonia. The product is separated by crystallization from dilute alcohol.

Sexton, U.S. Pat. No. 2,693,488, teaches that aminoalkanesulfonic acids are prepared by reacting an aqueous solution of ammonium hydroxide or an alkylamine with the metallic salt of the corresponding hydroxyalkanesulfonic acid.

The foregoing prior art processes described have several disadvantages. Some of the processes prepare salts as by-products. Many of the processes involve complex syntheses. The prior art processes usually result in low yields of the product. Furthermore, the reactants used are quite expensive, which makes commercial use of the 2-aminoethanesulfonic acid very costly.

What is needed is a process for the preparation of 2-aminoalkanesulfonic acids in which salts are not produced as by-products. What is further needed is a process which is relatively simple that gives high yields of products. Furthermore, a process in which the reactants are relatively inexpensive is needed.

SUMMARY OF THE INVENTION

The invention is a process for the preparation of the metal salt of 2-aminoalkanesulfonic acid which comprises contacting a 2-oxazolidinone with a water-soluble metal sulfite or a water-soluble metal hydrogen sulfite in aqueous solution under conditions such that a metal salt of 2-aminoethanesulfonic acid is prepared.

This process has significant advantages over the prior art processes. The process is relatively simple, gives high yields of products and no salt by-product is formed. Furthermore, the reactants are relatively inexpensive.

DETAILED DESCRIPTION OF THE INVENTION

In the process of this invention, 2-oxazolidinones are reacted with metal sulfites or metal hydrogen sulfites. 2-Oxazolidinones useful in this process include those corresponding to formula I

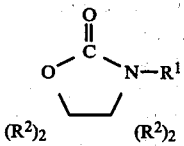

wherein:

$R^1$ is separately in each occurrence hydrogen, $C_{1-20}$ hydrocarbyl and $C_{1-20}$ hydroxyhydrocarbyl; and $R^2$ is hydrogen and $C_{1-20}$ hydrocarbyl.

$C_{1-20}$ hydrocarbyl means herein an organic radical containing between 1 and 20 carbon atoms to which are bonded hydrogen atoms. Included are the following groups: $C_{1-20}$ alkyl, $C_{1-20}$ alkenyl, $C_{1-20}$ alkynyl, $C_{3-20}$ cycloalkyl, $C_{3-20}$ cycloalkenyl, $C_{6-20}$ aryl, $C_{7-20}$ alkaryl or $C_{7-20}$ aralkyl.

$C_{1-20}$ hydroxyhydrocarbyl means herein a hydrocarbyl group which is hydroxy-substituted.

The term aryl refers herein to biaryl, phenyl, naphthyl, phenanthyl and anthranyl. Alkaryl refers herein to an alkyl-, alkenyl- or alkynyl-substituted aryl substituent wherein aryl is as defined hereinbefore. Aralkyl means herein an alkyl, alkenyl or alkynyl substituent substituted with an aryl group, wherein aryl is as defined hereinbefore. $C_{1-20}$ alkyl includes straight and branched chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-20}$ alkenyl includes straight and branched chain ethenyl, propenyl, butenyl, pentenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl groups. $C_{1-20}$ alkynyl groups include straight and branched chain ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl and eicosynyl groups.

$C_{3-20}$ cycloalkyl refers to an alkyl group containing one, two, three or more cyclic rings, including cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, bicyclopropyl, bicyclobutyl, bicyclopentyl, bicyclohexyl, bicycloheptyl, bicyclooctyl, bicyclononyl, bicyclodecyl, tricyclopropyl, tricyclobutyl, tricyclopentyl, tricyclohexyl groups and groups containing two or more of the cycloalkyl groups named hereinbefore. $C_{3-20}$ cycloalkenyl refers to mono-, di- and polycyclic groups containing one or more double bonds including cyclopropenyl, cyclobutenyl, cyclopentenyl, cyclohexenyl, cycloheptenyl, cyclooctenyl, cyclononenyl, cyclodecenyl, cycloundecenyl, cyclododecenyl, cyclotridecenyl, cyclotetradecenyl, cyclopentadecenyl, cyclohexadecenyl, cycloheptadecenyl, cyclooctadecenyl, cyclononadecenyl, cycloeicosenyl, bicyclopropenyl, bicyclobutenyl, bicyclopentenyl, bicycloheptenyl, bicyclooctenyl, bicyclononenyl, bicyclopentenyl, tricyclopropenyl, tricyclobutenyl, tricyclopentenyl, tricyclohexenyl groups. $C_{3-20}$ cycloalkenyl also refers to the above named cycloalkenyl groups wherein two or more double bonds are present, for example, cyclobutadienyl, cyclopentadienyl and cyclohexadienyl groups.

In this invention, $R^1$ is preferably hydrogen, $C_{1-20}$ alkyl, $C_{6-20}$ aryl or $C_{1-20}$ hydroxyalkyl; more preferably hydrogen, $C_{1-10}$ lower alkyl, or $C_{1-10}$ lower hydroxyalkyl; even more preferably hydrogen, methyl, ethyl or 2-hydroxyethyl; and most preferably hydrogen. $R^2$ is preferably hydrogen, $C_{1-20}$ alkyl, $C_{1-20}$ alkenyl, $C_{1-20}$ alkynyl, $C_{6-20}$ aryl, or $C_{7-20}$ aralkyl; more preferably hydrogen, $C_{1-10}$ lower alkyl, phenyl or benzyl; even more preferably hydrogen, methyl, ethyl or phenyl; and most preferably hydrogen.

In this process any water-soluble metal sulfite or water-soluble metal hydrogen sulfite is useful. Preferable metal sulfite and metal hydrogen sulfites are alkaline or alkali metal sulfites or alkaline or alkali metal hydrogen sulfites. More preferable metal sulfites and metal hydrogen sulfites are the alkali metal sulfites and the alkali metal hydrogen sulfites, with sodium sulfites and sodium hydrogen sulfites most preferred. Alkali metal refers herein to lithium, sodium, potassium, rubidium, cesium and francium. Alkaline metal refers herein to beryllium, magnesium, calcium, strontium, barium and radium.

Metal as used herein refers to any metal which forms a sulfite or hydrogen sulfite salt when contacted with sulfurous acid.

The metal salt of 2-aminoalkanesulfonic acid prepared by this process corresponds to formula II

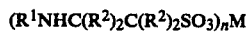

$$(R^1NHC(R^2)_2C(R^2)_2SO_3)_nM \qquad \text{II}$$

wherein $R^1$ and $R^2$ are as previously defined, M is any metal which forms a salt when contacted with sulfurous acid and n is 1, 2 or 3 depending upon the valence of M.

The process of this invention may be better understood by reference to equation I:

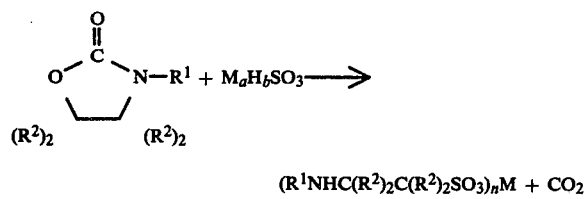

wherein $R^1$, $R^2$, M and n are as previously defined, a is an integer of 1 or 2 and b is an integer of 0 or 1 with the proviso that a+b is 2.

In this process, the 2-oxazolidinone is contacted with a water-soluble metal sulfite or water-soluble metal hydrogen sulfite in aqueous solution under conditions such that a metal salt of 2-aminoalkanesulfonic acid is prepared.

In this process any ratio of reactants will produce some product. A desirable ratio of 2-oxazolidinones to the water-soluble metal sulfite or metal hydrogen sulfite is between about 10:1 and 1:10. As this is a stoichiometric reaction, a 1:1 ratio of reactants is usually used. The use of a slight excess of the metal sulfite or metal hydrogen sulfite is advantageous so as to insure complete conversion of the oxazolidinone to products.

The solvent is water. Sufficient water to dissolve the reactants is a suitable amount of water. Generally, a desirable amount of water is that amount which has a weight ratio to the reactants of between about 1:1 and 5:1. It is preferable to use the lowest amount of water possible so as to reduce the costs of recovery of the product.

Mixed solvents can also be used in this invention. Such solvents would comprise water and any other solvent which is miscible with water. Examples include alkylene glycols, alkylene glycol ethers, lower alkanols and ethers.

Suitable temperatures for this process are those at which the reaction proceeds. Preferable temperatures are between 20° C. and 150° C. More preferable temperatures are between about 100° C. and 130° C. Below 100° C. the reaction is slow and above 130° C. the water distills off too rapidly.

Suitable reaction times are those at which a reasonable conversion of reactants to products can be achieved. It is preferable that reaction times be greater than 4 hours, more preferably between about 4 and 20 hours and most preferably between 8 and 10 hours.

The product is recovered by distilling off most of the aqueous solvent and adding any alkanol, preferably methanol, to precipitate the product. Any unreacted sulfite will remain in the aqueous solution, while any unreacted 2-oxazolidinone will dissolve in the alkanol solution.

In order to convert the metal salt of the 2-aminoalkanesulfonic acid to the acid form, an aqueous solution of the salt is treated with a nonorganic acid. Such inorganic acids include hydrochloric acid, sulfuric acid, nitric acid, phosphoric acid and the like.

This process usually results in greater than 90 percent conversion of the 2-oxazolidinones to the metal salts of aminoalkanesulfonic acid.

In one preferred embodiment of this invention, an oxazolidinone corresponding to formula I wherein $R^1$ and $R^2$ are hydrogen is reacted with a sodium sulfite or sodium hydrogen sulfite to prepare the sodium salt of 2-aminoethanesulfonic acid.

SPECIFIC EMBODIMENTS

The following examples are included for illustrative purposes only and do not limit the scope of the invention or claims.

EXAMPLE 1

A solution of 8.7 g (0.1 mole) of 2-xoazolidinone and 11.5 g (0.11 mole) of sodium hydrogen sulfite in 50 ml of water is heated to between about 100° C. and 105° C. for about 5 hours. The reaction mixture is heated to 130° C. for about 1 hour to distill off most of the water.

The crude product mixture weighs 15.5 g. This mixture is dissolved in about 20 ml of water, followed by the addition of 100 ml of methanol to precipitate the sodium salt of 2-aminoethanesulfonic acid. Filtration gives 7.08 g of white crystals which are soluble in water but insoluble in methanol and acetone. Infrared and nuclear magnetic resonance spectra show a product which is consistent with the structure of 2-aminoethanesulfonic acid.

EXAMPLE 2

A solution of 43.5 g of 2-oxazolidinone and 57.2 g of sodium hydrogen sulfite in 100 ml of water are heated to between 100° C. and 110° C. The solution becomes clear after a few minutes of heating. It turns cloudy as the temperature reaches 100° C. The total heating time is 4 hours. Water is removed on a rotary evaporator under vacuum to yield 83.5 g of a wet reaction product mixture.

The solid material is triturated with 100 ml of methanol and filtered. The solid recovered is further washed with 150 ml of methanol. The solid recovered which weighed 37.36 g contained the sodium salt of 2-aminoethanesulfonic acid.

EXAMPLE 3

The sodium salt of 2-aminoethanesulfonic acid (80 g) is triturated with 60 ml of concentrated hydrogen chloride. Thereafter 500 ml of methanol is added. The solid precipitate is filtered and washed with 400 ml of a 90 percent methanol solution. The product is 2-aminoethanesulfonic acid.

EXAMPLE 4

2-Oxazolidinone (13.5 g) and sodium hydrogen sulfite (15.6 g) is dissolved in 150 ml of water and heated at temperatures of between 100° C. and 105° C. for about 4 hours. Thereafter, 125 ml of water is distilled from the reaction mixture. The remaining mixture is heated for 2 more hours. Methanol (150 ml) is added after the reaction mixture is cooled to room temperature. Filtration yields a white crystalline product, 16.9 g. The product is washed with 100 ml of methanol.

The filtrate is evaporated to about 10-15 ml on a rotary evaporator under reduced pressure. Then 100 ml of methanol is added, the mixture is filtered to yield 1.85 g of product. The yield of the sodium salt of 2-aminoethanesulfonic acid is 85 percent.

What is claimed is:

1. A process for the preparation of the metal salt of 2-aminoalkanesulfonic acid which comprises contacting a 2-oxazolidinone with a water-soluble metal sulfite or a water-soluble metal hydrogen sulfite in aqueous solution or in a mixed solvent system comprising water and a water-miscible solvent, under conditions such that a metal salt of 2-aminoethanesulfonic acid is prepared.

2. The process of claim 1 wherein the 2-oxazolidinone corresponds to the formula

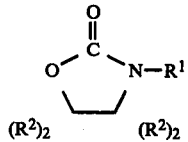

wherein $R^1$ is separately in each occurrence hydrogen, $C_{1-20}$ hydrocarbyl or $C_{1-20}$ hydroxyhydrocarbyl; and $R^2$ is separately in each occurrence hydrogen or $C_{1-20}$ hydrocarbyl.

3. The process of claim 2 wherein $R^1$ is hydrogen, $C_{1-20}$ alkyl, $C_{6-20}$ aryl or $C_{1-20}$ hydroxyalkyl.

4. The process of claim 3 wherein $R^1$ is hydrogen, $C_{1-10}$ lower alkyl or $C_{1-10}$ lower hydroxy alkyl.

5. The process of claim 3 wherein $R^1$ is hydrogen, methyl, ethyl or 2-hydroxyethyl.

6. The process of claim 2 wherein $R^1$ is hydrogen.

7. The process of claim 2 wherein $R^2$ is hydrogen, $C_{1-20}$ alkyl, $C_{1-20}$ alkenyl, $C_{1-20}$ alkynyl, $C_{6-20}$ aryl or $C_{7-20}$ aralkyl.

8. The process of claim 2 wherein $R^2$ is hydrogen, $C_{1-10}$ lower alkyl, phenyl or benzyl.

9. The process of claim 2 wherein $R^2$ is hydrogen, methyl, ethyl or phenyl.

10. The process of claim 2 wherein $R^2$ is hydrogen.

11. The process of claim 1 wherein the metal sulfite or metal hydrogen sulfite is an alkali or alkaline metal sulfite or alkali or alkaline metal hydrogen sulfite.

12. The process of claim 1 wherein the metal sulfite or metal hydrogen sulfite is an alkali metal sulfite or alkali metal hydrogen sulfite.

13. The process of claim 1 wherein the metal sulfite or metal hydrogen sulfite is a sodium sulfite or a sodium hydrogen sulfite.

14. The process of claim 1 wherein the temperature is between about 20° C. and 150° C.

15. The process of claim 1 wherein the temperature is between about 100° C. and 130° C.

16. The process of claim 1 which further includes contacting the metal salt of the 2-aminoethanesulfonic acid with an inorganic acid under conditions such that the 2-aminoethanesulfonic acid is prepared.

17. The process of claim 2 wherein $R^1$ is hydrogen and $R^2$ is hydrogen.

* * * * *

UNITED STATES PATENT AND TRADEMARK OFFICE
CERTIFICATE OF CORRECTION

PATENT NO. : 4,444,694
DATED : April 24, 1984
INVENTOR(S) : Hsin H. Hsieh

It is certified that error appears in the above-identified patent and that said Letters Patent are hereby corrected as shown below:

Col. 4, line 66, "2-xoazolidinone" should read
-- 2-oxazolidinone --.

Signed and Sealed this

Nineteenth Day of February 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,444,694

DATED : April 24, 1984

INVENTOR(S) : Hsin H. Hsieh

It is certified that error appears in the above-identified patent and that said Letters Patent is hereby corrected as shown below:

Col. 2, lines 21-28, delete present formula and replace with:

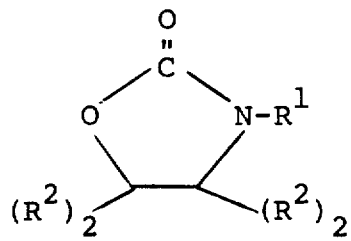

Column 3, lines 60-67, delete present formula and replace with:

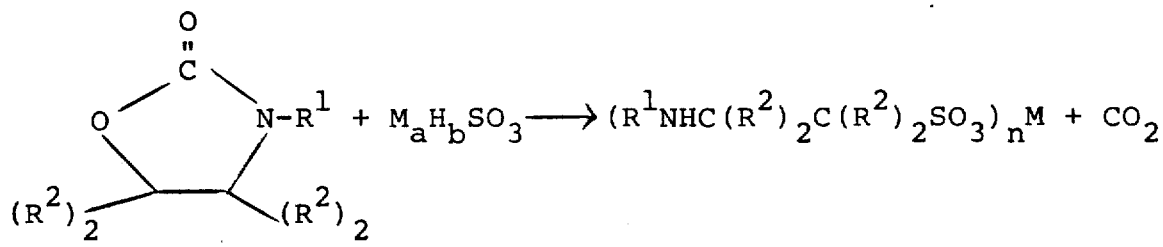

UNITED STATES PATENT AND TRADEMARK OFFICE
CERTIFICATE OF CORRECTION

PATENT NO. : 4,444,694

DATED : April 24, 1984

INVENTOR(S) : Hsin H. Hsieh

It is certified that error appears in the above-identified patent and that said Letters Patent is hereby corrected as shown below:

Col. 6, lines 8-14, delete present formula and replace with:

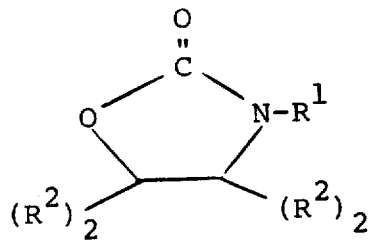

Signed and Sealed this

Fourteenth Day of May 1985

[SEAL]

Attest:

DONALD J. QUIGG

Attesting Officer    Acting Commissioner of Patents and Trademarks